(12) United States Patent
Kitamura

(10) Patent No.: US 11,968,484 B2
(45) Date of Patent: Apr. 23, 2024

(54) INFORMATION MANAGEMENT SYSTEM, AND METHOD FOR DEVICE REGISTRATION OF MEASURING DEVICE AND INFORMATION TERMINAL

(71) Applicant: OMRON HEALTHCARE Co., Ltd., Kyoto (JP)

(72) Inventor: Takashi Kitamura, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 255 days.

(21) Appl. No.: 17/448,145

(22) Filed: Sep. 20, 2021

(65) Prior Publication Data

US 2022/0007091 A1 Jan. 6, 2022

Related U.S. Application Data

(63) Continuation of application No. PCT/JP2020/009231, filed on Mar. 4, 2020.

(30) Foreign Application Priority Data

Mar. 25, 2019 (JP) ................................ 2019-056951

(51) Int. Cl.
H04Q 9/00 (2006.01)
G16H 10/60 (2018.01)
H04B 11/00 (2006.01)

(52) U.S. Cl.
CPC ............... *H04Q 9/00* (2013.01); *G16H 10/60* (2018.01); *H04B 11/00* (2013.01); *H04Q 2209/40* (2013.01)

(58) Field of Classification Search
CPC ...... H04Q 9/00; H04Q 2209/40; G16H 10/60; H04B 11/00; A61B 5/0015; A61B 5/02225; H04M 1/72412; G06F 21/44
See application file for complete search history.

(56) References Cited

U.S. PATENT DOCUMENTS 10,285,052 B2 * 5/2019 Modzelewski ....... H04W 12/04
2018/0152837 A1 5/2018 Modzelewski et al.
(Continued)

FOREIGN PATENT DOCUMENTS

CN 105122706 A 12/2015
CN 113544476 A * 10/2021 ............. G16H 10/60
(Continued)

OTHER PUBLICATIONS

Translation of CN105122706 (Year: 2015).*

(Continued)

*Primary Examiner* — Daniel Pihulic
(74) *Attorney, Agent, or Firm* — Birch, Stewart, Kolasch & Birch, LLP

(57) ABSTRACT

In an information management system according to the present invention, a measuring device including an output means including an oscillation device capable of generating ultrasonic waves causes the oscillation device to generate ultrasonic waves including identification information enabling the measuring device to be identified. An information terminal including a microphone capable of detecting the ultrasonic waves acquires the identification information from the ultrasonic waves via the microphone. The information terminal is caused to display the measuring device for which the identification information has been acquired. In a case where the information terminal receives an input indicating that the displayed measuring device is to be device-registered, the measuring device is device-registered on the information terminal.

12 Claims, 12 Drawing Sheets

(56) References Cited

U.S. PATENT DOCUMENTS

| | | | | |
|---|---|---|---|---|
| 2022/0007091 A1* | 1/2022 | Kitamura | ................ | G06F 21/44 |
| 2022/0071569 A1* | 3/2022 | Kitamura | ............... | G16H 50/20 |

FOREIGN PATENT DOCUMENTS

| | | | | | |
|---|---|---|---|---|---|
| DE | 112020000686 T5 | * | 11/2021 | ............. | G16H 10/60 |
| DE | 112020000684 T5 | * | 2/2022 | ......... | A61B 5/02233 |
| JP | 2007-249425 A | | 9/2007 | | |
| JP | 2015-191076 A | | 11/2015 | | |
| JP | 2016-512965 A | | 5/2016 | | |
| JP | 2017-170108 A | | 9/2017 | | |
| JP | 2018023016 A | * | 2/2018 | | |
| JP | 2020160589 A | * | 10/2020 | ............. | G16H 10/60 |
| JP | 2020160620 A | * | 10/2020 | ......... | A61B 5/02233 |
| WO | 2014/147713 A1 | | 9/2014 | | |
| WO | 2019/031330 A1 | | 2/2019 | | |
| WO | WO-2020195652 A1 | * | 10/2020 | ......... | A61B 5/02233 |
| WO | WO-2020195653 A1 | * | 10/2020 | ............. | G16H 10/60 |

OTHER PUBLICATIONS

International Search Report for International Application No. PCT/JP2020/009231, dated Jun. 16, 2020.

German Office Action for German Application No. 11 2020 000 666.7, dated May 3, 2023, with an English translation.

Chinese Office Action and Search Report for corresponding Chinese Application No. 202080019494.1, dated Nov. 22, 2023, with English translation.

* cited by examiner

[FIG. 1]
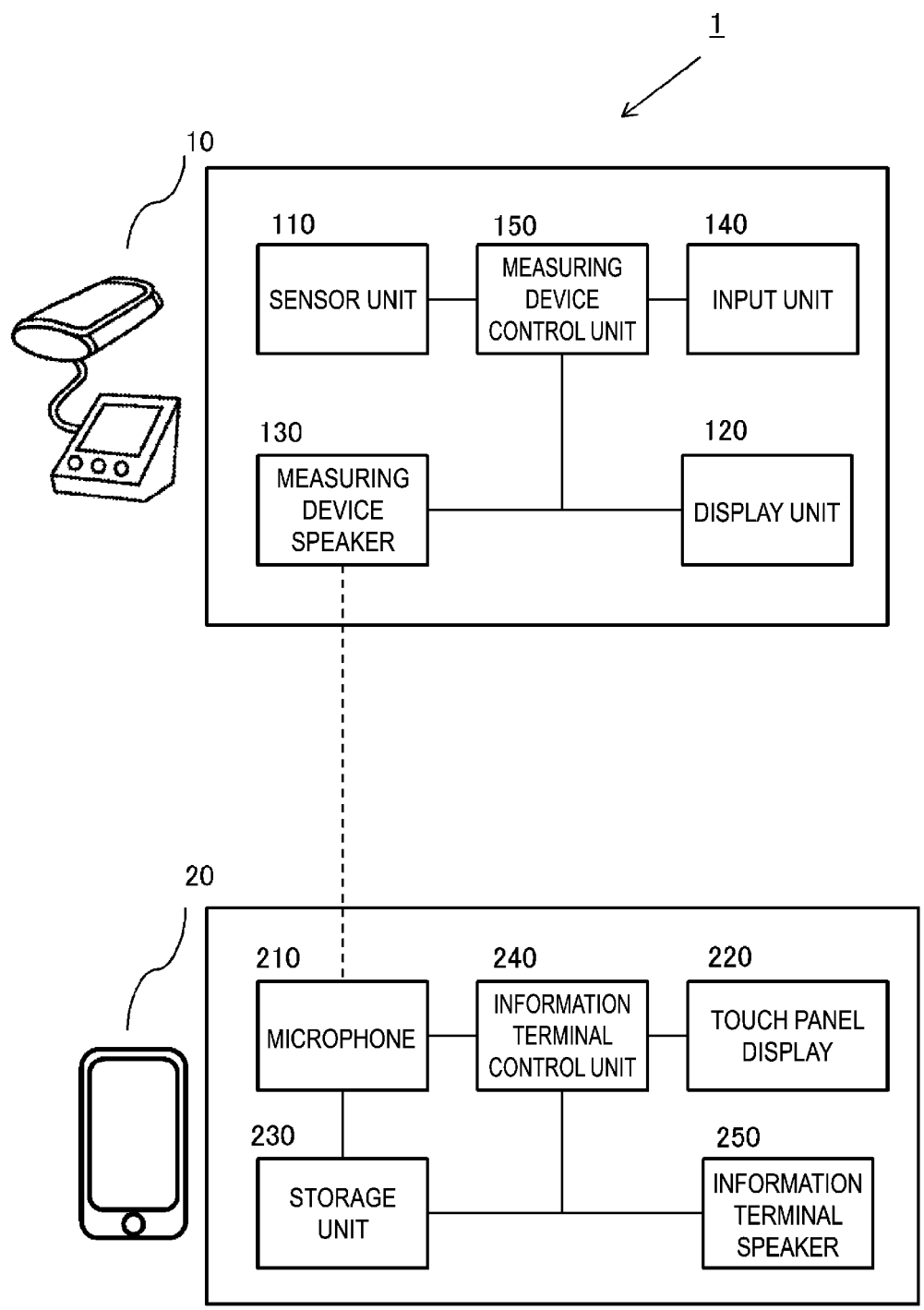

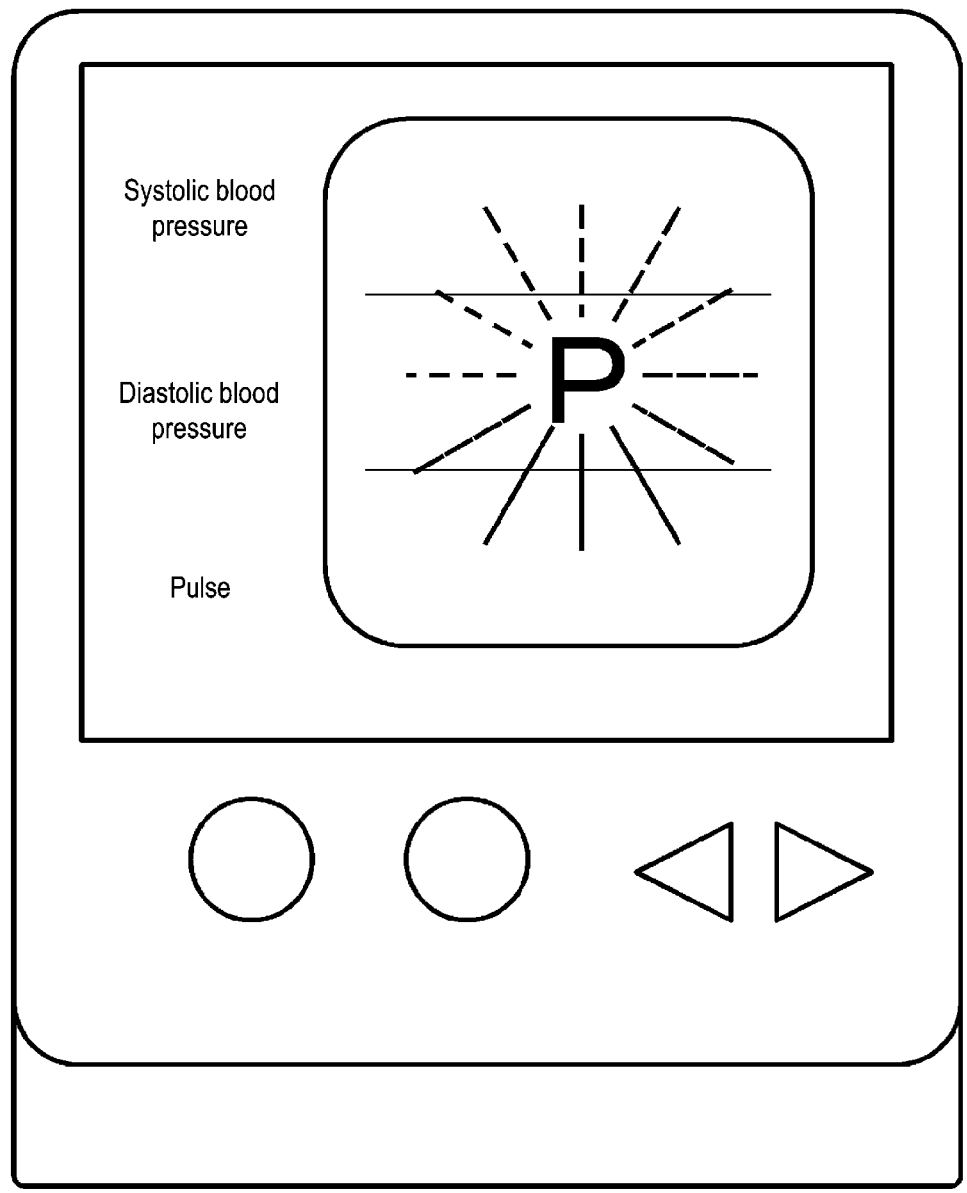
[FIG. 2]

[FIG. 3]
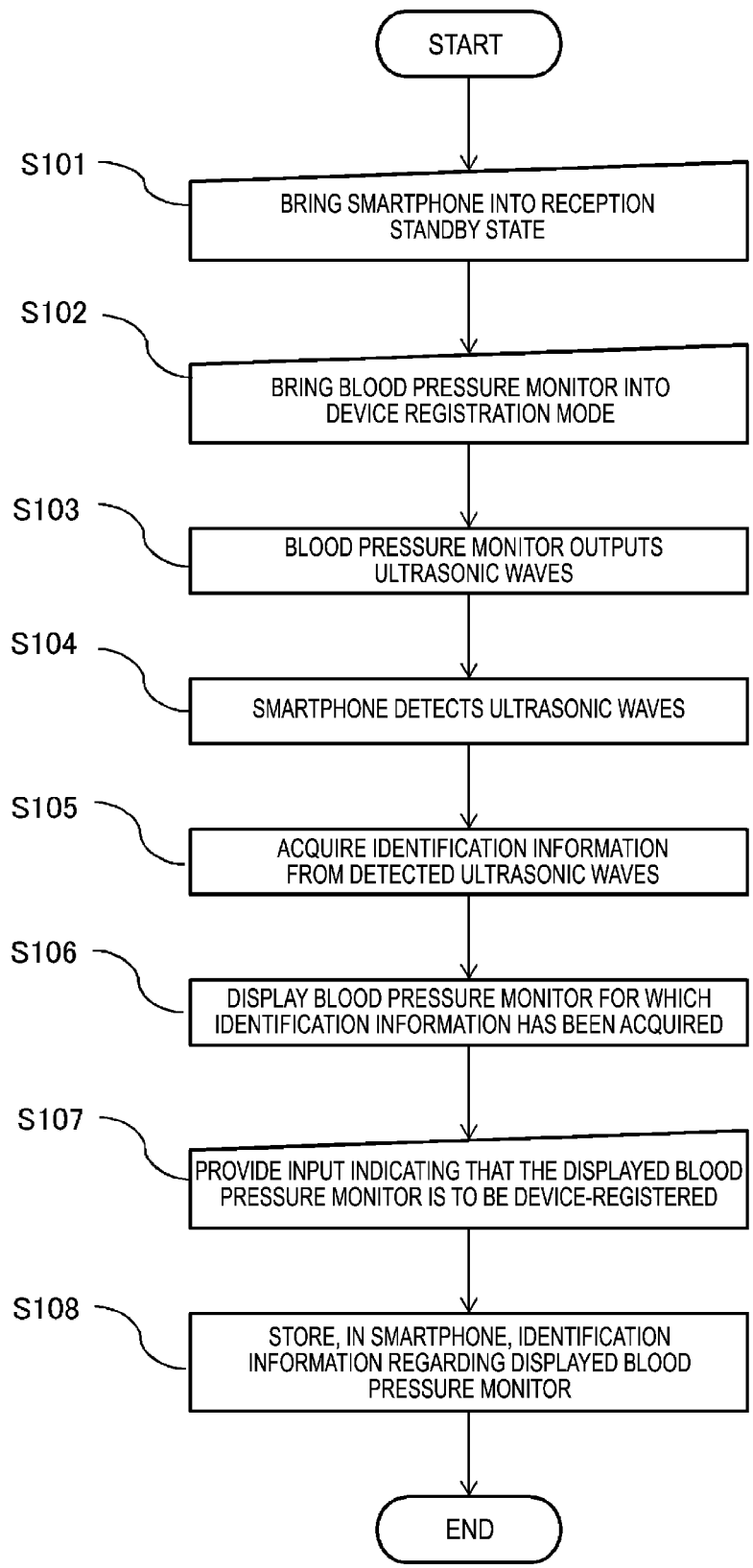

[FIG. 4]
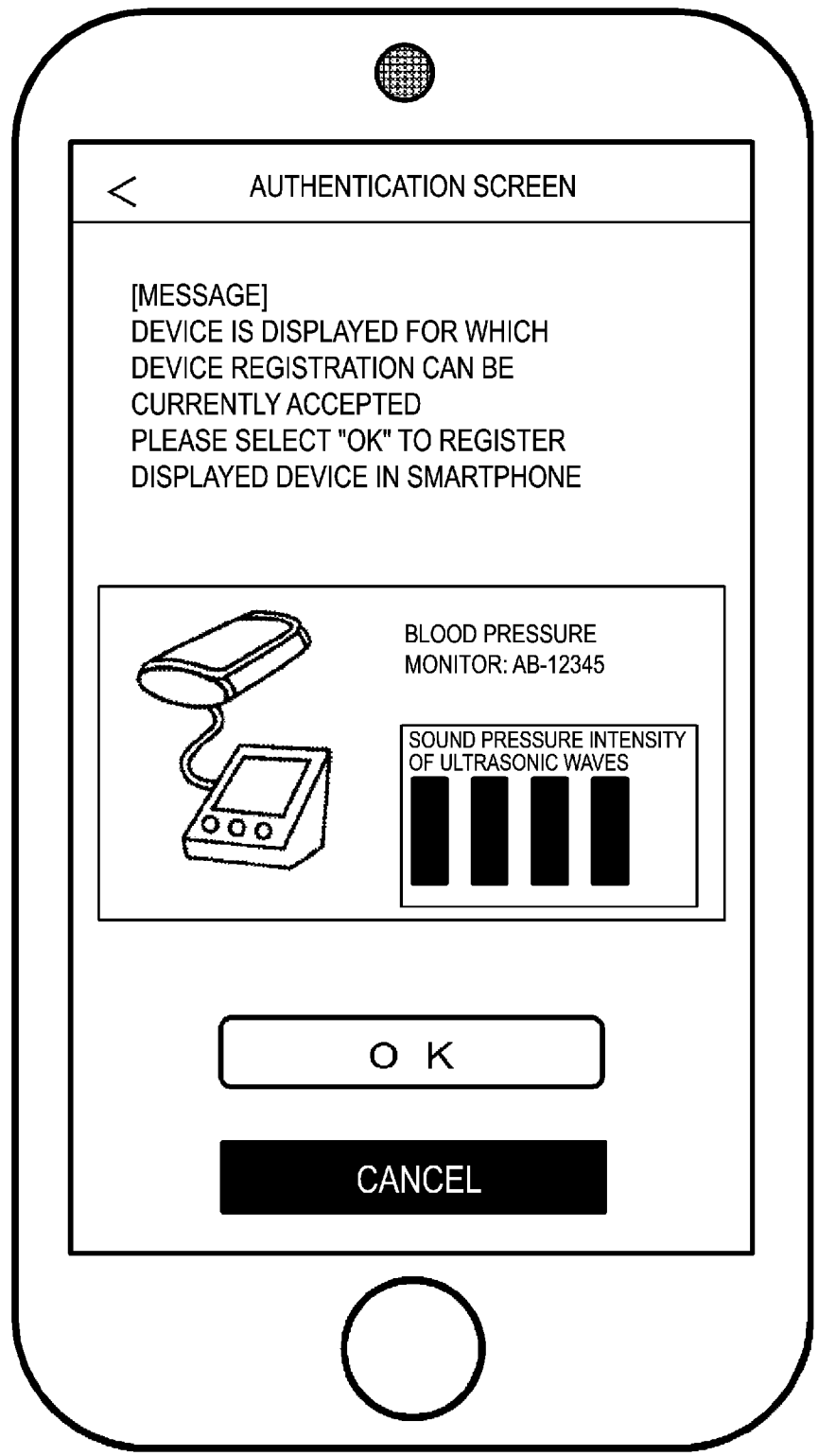

[FIG. 5]
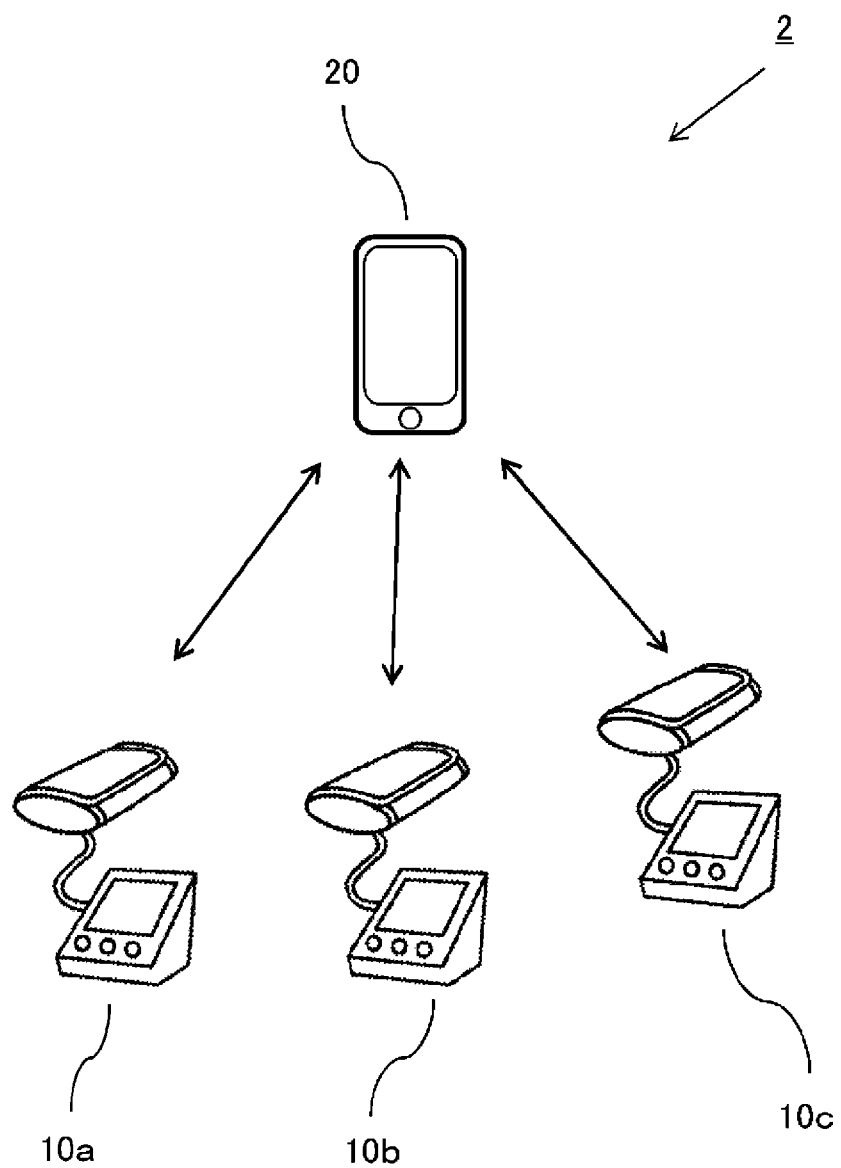

[FIG. 6]
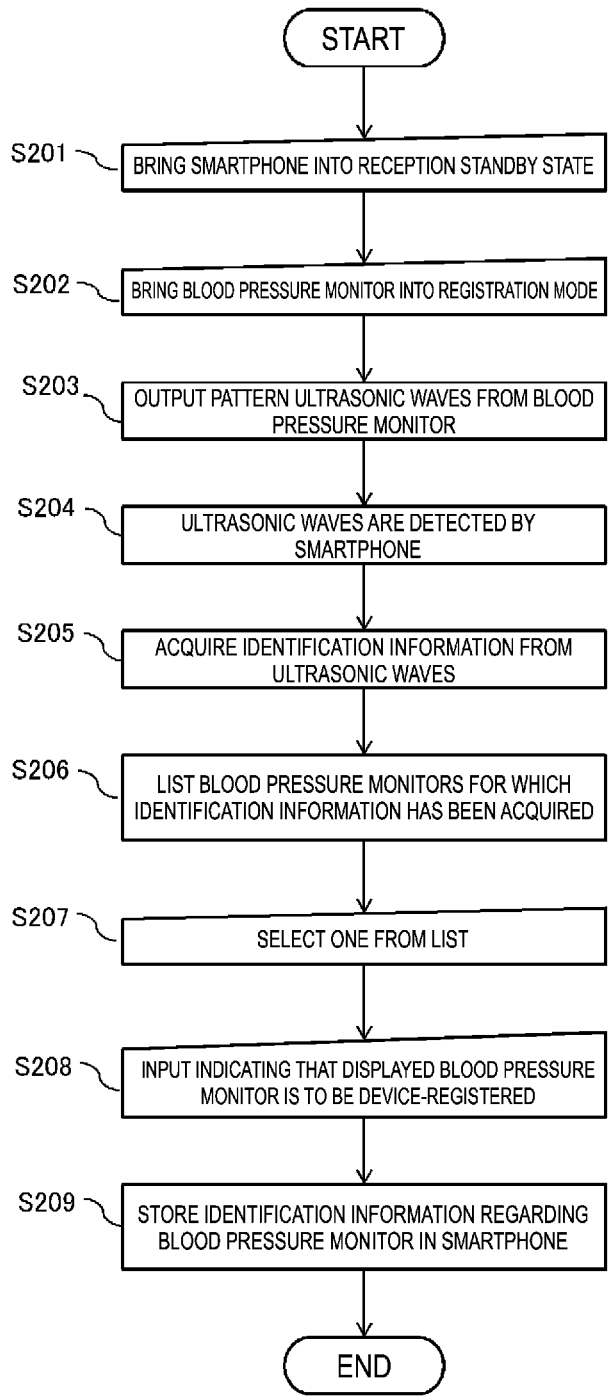

[FIG. 7]
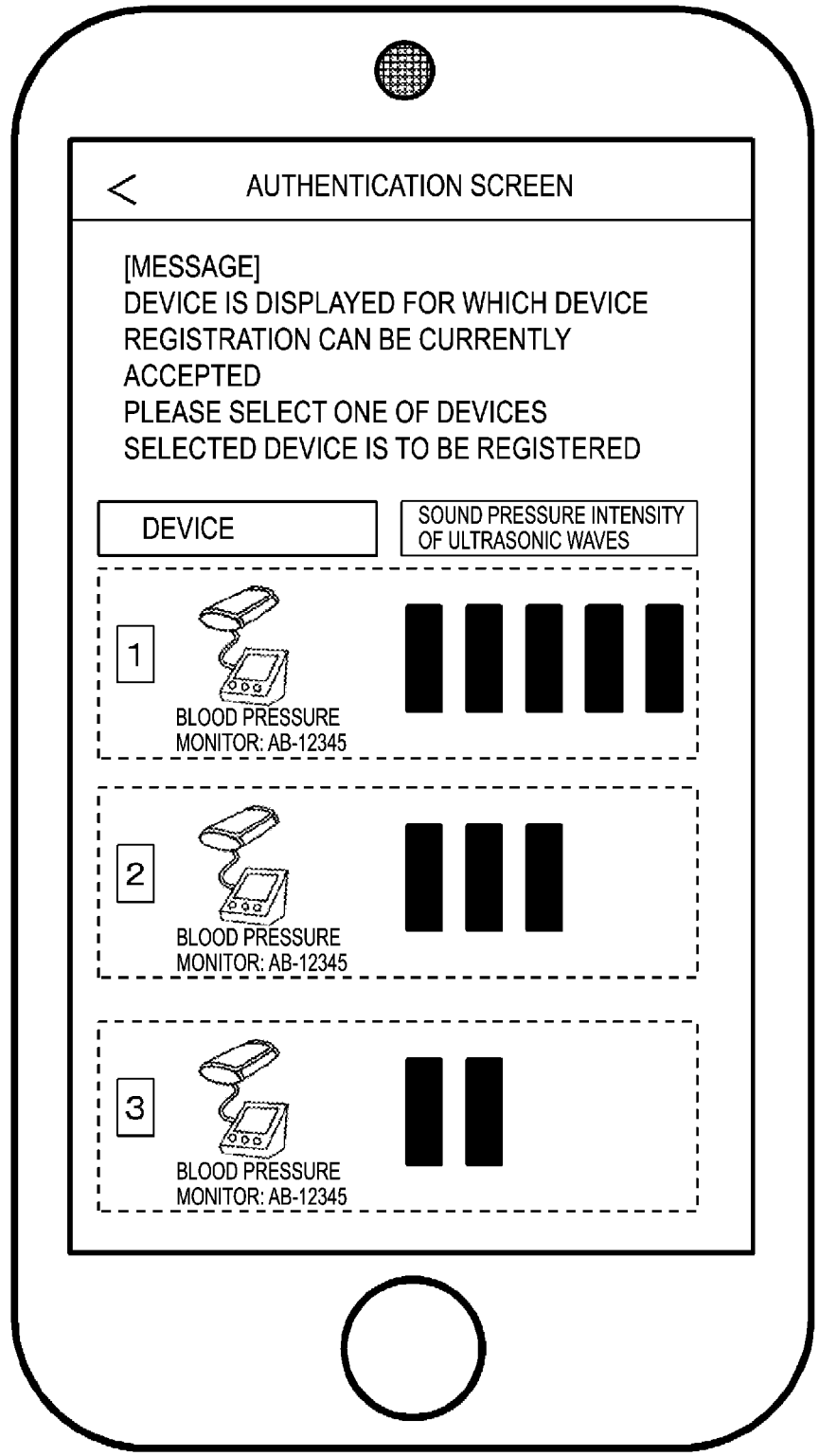

[FIG. 8]
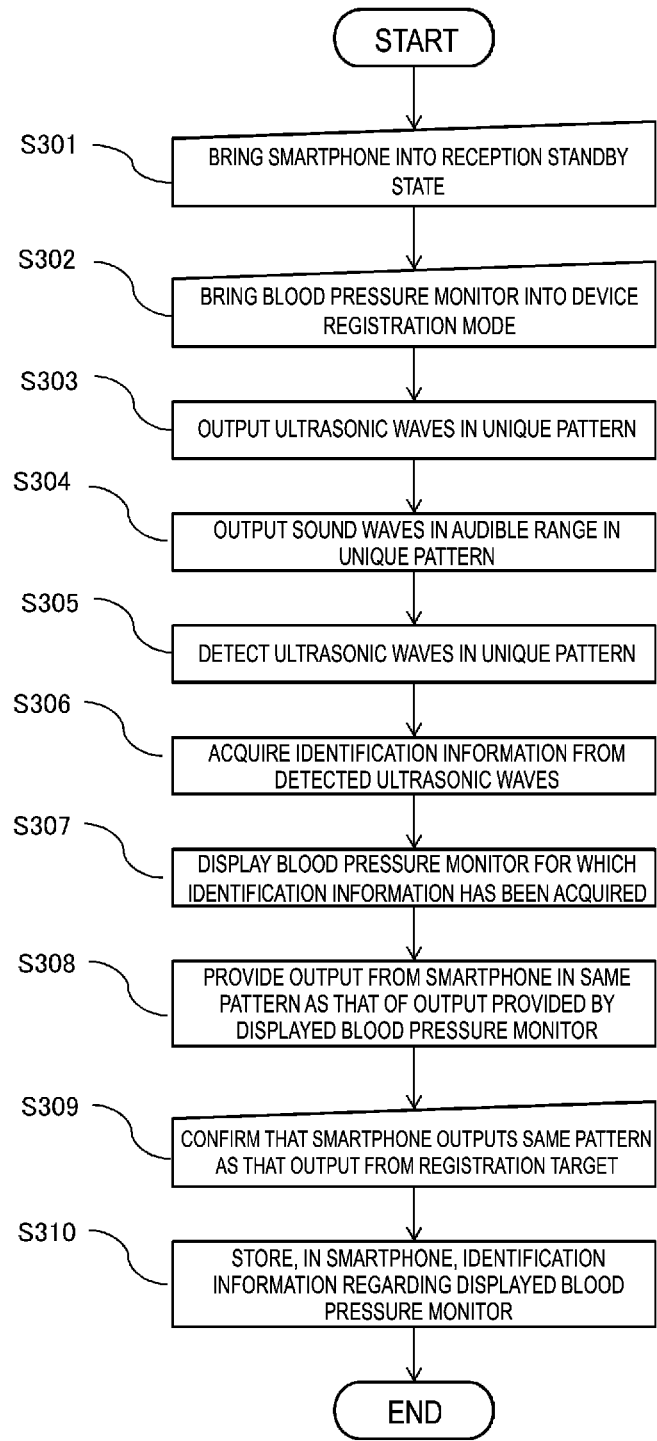

[FIG. 9]
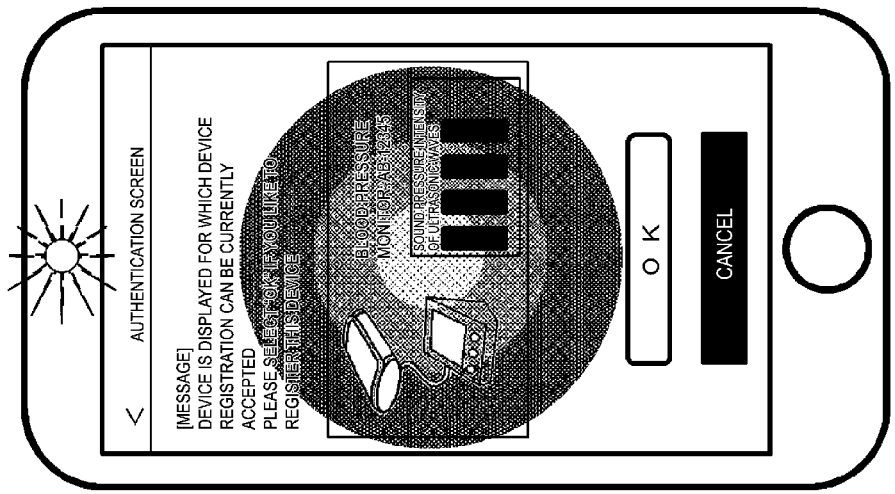
(B)
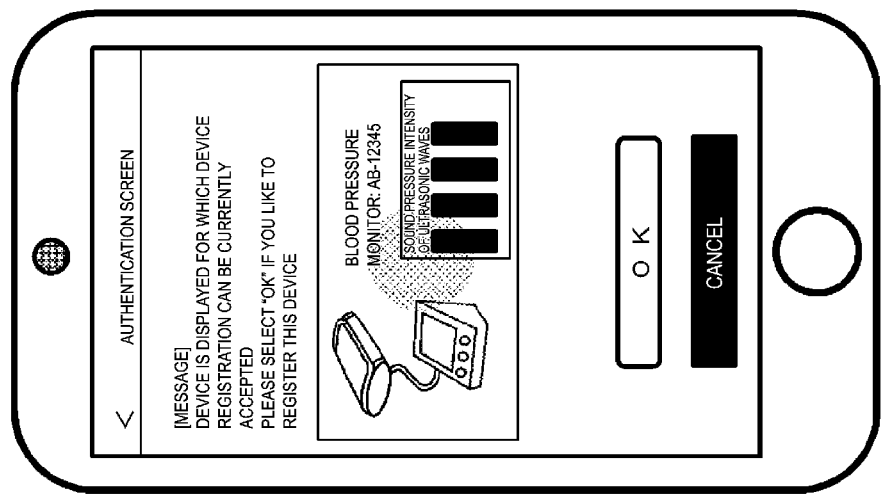
(A)

[FIG. 10]
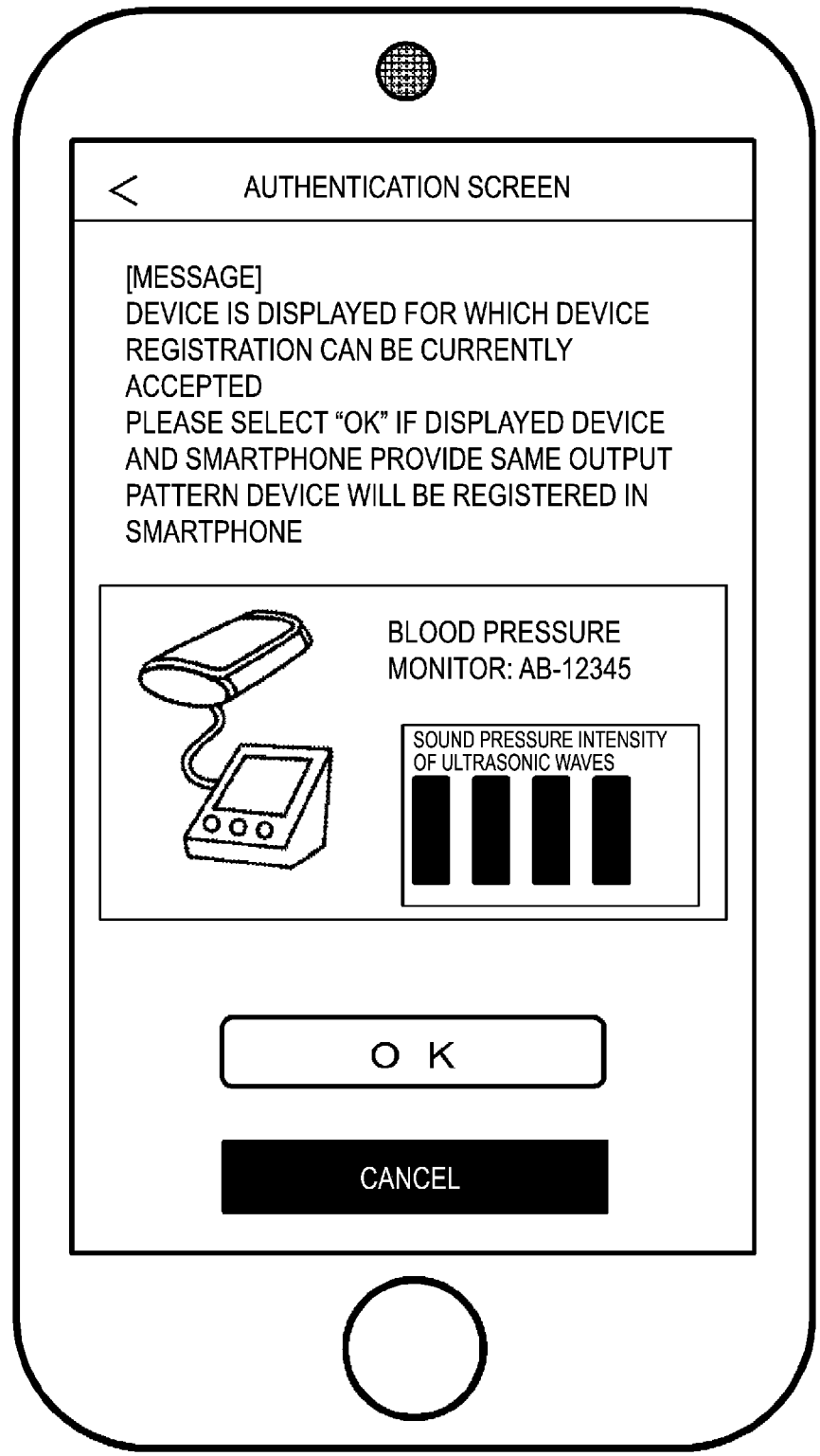

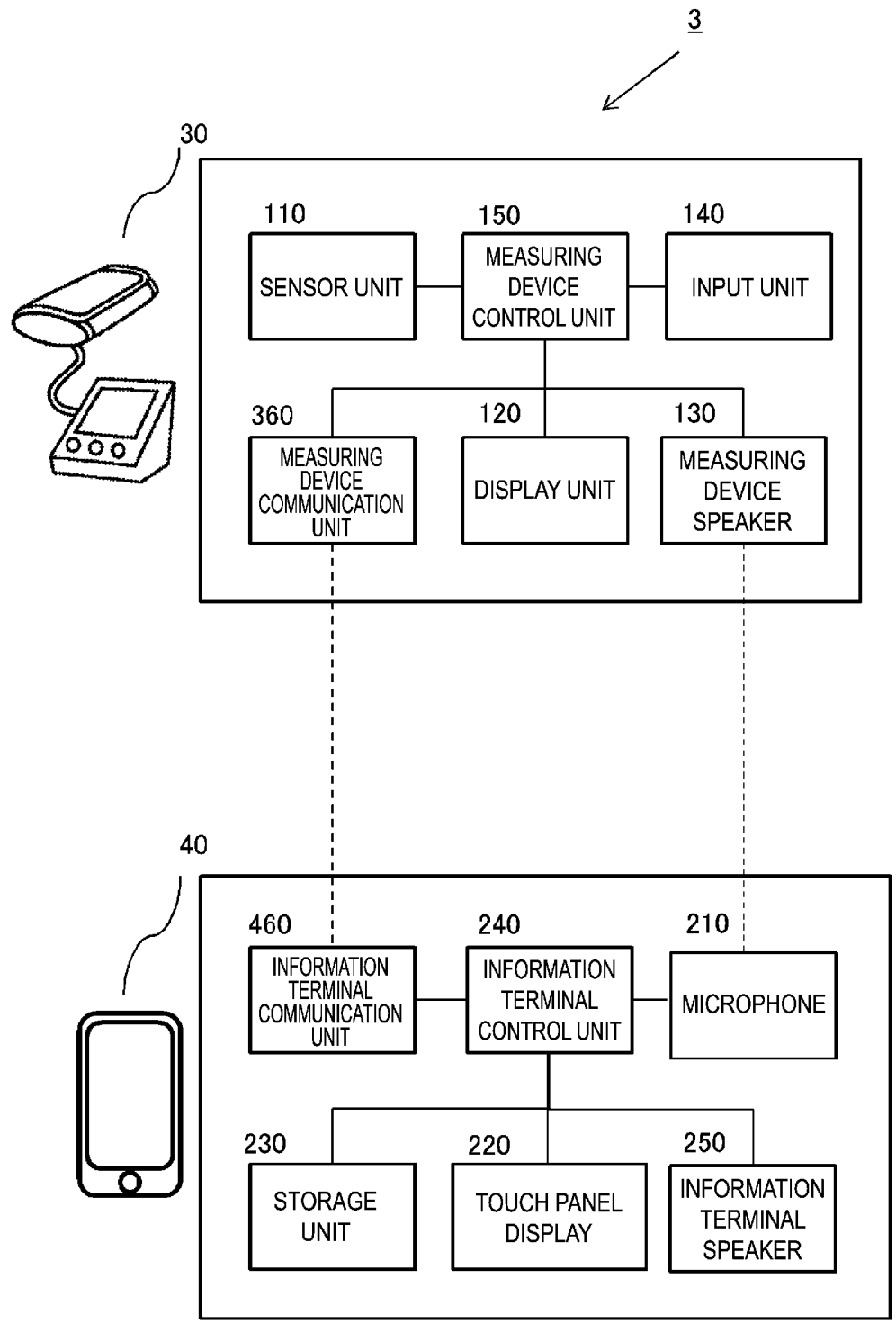
[FIG. 11]

[FIG. 12]

| OUTPUT PATTERN | | | | | | | | | | | | | | | | | | | |
|---|---|---|---|---|---|---|---|---|---|---|---|---|---|---|---|---|---|---|---|
| DEVICE 1 | ■ | ■ | ■ | ■ | | ■ | ■ | ■ | | ■ | ■ | | ■ | ■ | ■ | | ■ | ■ | |
| DEVICE 2 | ■ | ■ | ■ | ■ | ■ | ■ | | ■ | ■ | | ■ | ■ | | ■ | ■ | ■ | | | |
| DEVICE 3 | ■ | ■ | | ■ | | ■ | ■ | ■ | | ■ | ■ | ■ | ■ | | ■ | ■ | | ■ | ■ |

INFORMATION MANAGEMENT SYSTEM, AND METHOD FOR DEVICE REGISTRATION OF MEASURING DEVICE AND INFORMATION TERMINAL

CROSS-REFERENCE TO RELATED APPLICATIONS

This application is the U.S. national stage application filed pursuant to 35 U.S.C. 365(c) and 120 as a continuation of International Patent Application No. PCT/JP2020/009231, filed Mar. 4, 2020, which application claims priority to Japanese Patent Application No. 2019-056951, filed Mar. 25, 2019, which applications are incorporated herein by reference in their entireties.

TECHNICAL FIELD

The present invention relates to an information management system including a measuring device and an information terminal, and a method for device registration of the measuring device and the information terminal.

BACKGROUND ART

In recent years, it has become widespread to perform health management by: measuring personal health-related information (also referred to as "health information" hereinafter), such as weight, blood pressure value, and activity level, by a measuring device; and recording and analyzing the measurement results by an information terminal, such as a smartphone.

When such health management is performed, preferably the measuring device and the information terminal are connected to each other and the result of measurement by the measuring device can be automatically acquired by the information terminal without a user having to input the result to the information terminal each time. Specifically, for example, a method can be considered in which an information terminal receives measurement information from a measuring device by near-field wireless communication, but under circumstances in which a plurality of measuring devices of the same type are used, it is necessary to prevent erroneous reception of information from measuring devices other than the device that has actually performed the measurement.

In order to solve such problems, a predetermined measuring device may be device-registered in a predetermined information terminal, and information may be exclusively acquired from the device-registered measuring device. The device registration is performed by, for example, registering, in an information terminal, identification symbols identifying individual measuring devices, and conventionally a method has been adopted in which identification information printed on a housing of a device or on a seal attached to the housing is manually input to the information terminal.

With such a method, the task is complex for the user and may result in erroneous input. In contrast, Patent Document 1 proposes that serial information provided on a measuring device be acquired by a receiving device by taking a picture or scanning a code and that the serial information acquired be used for device registration.

Additionally, pairing (mutual authentication of devices) has spread that uses wireless communication based on Bluetooth (trade name) (for example, Patent Document 2). In a specific authentication method, pairing is performed such that one of the devices transmits, by advertisement, information indicating that the device is ready for pairing and such that the other device receives the information and designates the first device.

CITATION LIST

Patent Literature

Patent Document 1: JP 2016-512965 T
Patent Document 2: JP 2017-170108 A

SUMMARY OF INVENTION

Technical Problem

Nevertheless, even in the technology set forth in Patent Document 1 described above, the user must capture an image (or scan) the identification information and thus, in this regard, a complex task arises similarly to the related art. Furthermore, in the technology described in Patent Document 2, in a situation in which a plurality of devices of the same type transmit advertisement information indicating that the devices are ready for pairing, a user fails to determine which of candidates displayed on an information terminal is to be paired and fails to achieve proper pairing.

In light of the related art such as described above, an object of the present invention is to provide a technology that reduces a burden on a user when the user device-registers a measuring device in an information terminal.

Solution to Problem

In order to accomplish the object described above, the present invention provides an information management system including one or more measuring devices and one or more information terminals, wherein the measuring device includes: an output means including an oscillation device capable of generating at least ultrasonic waves; and a control means for using the ultrasonic waves generated by the oscillation device to transmit measuring device information including identification information identifying the measuring device, the information terminal includes: an input means including a microphone capable of detecting the ultrasonic waves, output means including at least a display means, a storage means, and a control means, the control means of the information terminal: acquires, via the microphone, the identification information from the ultrasonic waves output from the measuring device, causes the display means of the information terminal to display the measuring device having transmitted the identification information acquired, receives, via the input means, an input indicating that the measuring device displayed on the display means of the information terminal is to be registered on the information terminal, and causes the storage means to store the identification information regarding the measuring device for which the input indicating registration of the measuring device on the information terminal has been provided.

The measuring device described above includes various measuring devices such as: body information measuring devices such as a scale, a body composition meter, a blood pressure monitor, a heart rate monitor, and a thermometer; activity measuring devices such as a pedometer and an activity meter provided in various fitness devices; and environmental information measuring devices such as a temperature and humidity meter, a noise meter, and an illuminometer. Further, the information terminal described above includes mobile information terminals such as a smartphone, a tablet terminal, and a laptop computer as well as a stationary information terminals.

Note that for the identification information described above, a signal including the identification information may be superimposed on the ultrasonic waves for transmission, or the identification information may be represented by an output pattern of the ultrasonic waves.

According to such a configuration, an operation performed by the user to device-register the measuring device on the information terminal is only to bring the measuring device and the information terminal into a device registration state and to confirm the measuring device displayed on the information terminal, thus enabling a reduction in burden on the user. Additionally, even with a plurality of measuring devices of the same type, the intensity of sound pressure detected by the microphone correlates with a distance from an ultrasonic wave source, and thus based on an accurate estimation that a device outputting the ultrasonic wave in the most intense sound pressure is the closest device, a desired measuring device can be selected from a positional relationship between the information terminal and the plurality of measuring devices.

In addition, the measuring device information may include a measurement value obtained by the measuring device. With such a configuration, the data of the measurement value can also be transmitted using ultrasonic waves, and other communication means for data transmission can be omitted, thus enabling a reduction in the cost of the measuring device.

Additionally, in a case of acquiring the identification information regarding a plurality of the measuring devices, the control means of the information terminal may cause, in response to acquisition of the identification information, the display means to preferentially display the measuring device for which ultrasonic waves with a more intense sound pressure have been detected by the microphone.

In a case that the measuring device is registered on the information terminal, the operation is typically performed near the device to be registered. Thus, the configuration as described above allows the desired measuring device to be efficiently device-registered on the information terminal.

Additionally, the control means of the measuring device may generate the ultrasonic waves in a unique pattern and cause the output means of the measuring device to generate a human-perceivable output in a pattern identical to the unique pattern, the control means of the information terminal may: cause the output means of the information terminal to generate a human-perceivable output in a pattern identical to the pattern of the output from the measuring device displayed on the display means of the information terminal, and use, as the input indicating the registration of the measuring device on the information terminal, reception, via the input means, of an input indicating that an occurrence pattern of the output from the measuring device displayed on the display means of the information terminal is identical to an occurrence pattern of the output from the information terminal.

Note that "pattern" as used herein refers to the timing of the output, and does not mean the frequency of the ultrasonic waves. However, in a case where a plurality of measuring devices are present in the system, the ultrasonic waves emitted by the individual measuring devices may have different frequencies. FIG. 12 illustrates an image diagram of a "pattern" of the present specification. The horizontal axis of FIG. 12 represents the time axis. Black squares each indicate the presence of output.

Note that "unique" described above does not only indicates that a pattern specific to each device is defined in advance but means that at the time of pattern output, the device can be distinguished from the other devices. Thus, the pattern may be a random pattern created each time from an individual seed, an individual random number table, and the like for each device.

According to the configuration of the system as described above, the human-perceivable, predetermined pattern is simultaneously output by both the measuring device and the information terminal, and thus device registration can be achieved with easy determination of whether the device to be device-registered matches the device recognized by the information terminal.

Additionally, the output means of the measuring device may include a sound wave generating means capable of outputting sound waves in an audible range, and the control means of the measuring device may cause the sound wave generating means to output ultrasonic waves in the unique pattern and to generate the sound waves in the audible range in an identical pattern.

Such a configuration enables the user to auditorially check the pattern output by the measuring device even without viewing the measuring device, allowing the user to perform a device registration operation with focus placed only on the information terminal. This enables a reduction in complicatedness to the user.

Additionally, the measuring device may further include a display means, and the control means of the measuring device may cause the sound wave generating means to generate the ultrasonic waves in the unique pattern, and may vary display of the display means in a pattern identical to the unique pattern. Note that the display means as used herein also includes a light emitting means such as a flashlight, and the pattern may be generated by blinking of the light emitting means.

Such a configuration enables the user to perform the device registration operation by viewing both the measuring device and the information terminal, thus allowing the user to perform device registration even in a situation where generating sound is not appropriate.

Additionally, the control means of the information terminal may vary display of the display means of the information terminal in a pattern identical to the unique pattern. In addition, the display means herein may also include light emitting means such as a flashlight, and the pattern may be generated by blinking of the light emitting means.

Such a configuration allows the user to check the display means of the information terminal for device registration, while simultaneously checking the output pattern from the information terminal. Additionally, even in a situation where generating sound is not appropriate, device registration can be performed.

In addition, the output means of the information terminal may include sound wave generating means capable of generating sound waves in the audible range, and the control means of the information terminal may cause the sound wave generating means of the information terminal to generate the sound waves in the audible range in a pattern identical to the unique pattern. Such a configuration allows the user to check the pattern without viewing the information terminal.

Additionally, the output means of the information terminal may include a vibration device vibrating the information terminal, and the control means of the information terminal may cause the information terminal to vibrate in a pattern identical to the unique pattern.

Such a configuration allows the user to check the output pattern from the information terminal without viewing the information terminal even in a situation where generating sound is inappropriate.

Additionally, the measuring device and the information terminal may each include a wireless communication means capable of transmitting and receiving information from each other and device-register each other via the wireless communication means. In this regard, a communication scheme such as Bluetooth can be used for the wireless communication means.

According to such a configuration, pairing (mutual authentication) is established by bidirectional wireless communication, while the measuring device to be device-registered being searched for by ultrasonic communication, and bidirectional transmission and/or reception is subsequently performed.

A device registration method according to the present invention is a method for device registration of a measuring device on an information terminal, the method including the steps of: the measuring device generating ultrasonic waves to transmit measuring device information including identification information identifying the measuring device; the information terminal detecting the ultrasonic waves; the information terminal acquiring the identification information from the ultrasonic waves; the information terminal displaying the measuring device having transmitted the identification information acquired; the information terminal receiving an input indicating that the measuring device displayed is to be registered on the information terminal, and the information terminal storing the identification information regarding the measuring device for which the input indicating registration of the measuring device on the information terminal has been provided.

Advantageous Effects of Invention

According to the present invention, a burden on a user can be reduced when the user device-registers a measuring device in an information terminal.

BRIEF DESCRIPTION OF DRAWINGS

FIG. 1 is a block diagram illustrating an overview of a configuration example of an information management system according to a first embodiment.

FIG. 2 is a diagram illustrating an example of a display screen of a blood pressure monitor of the information management system according to the first embodiment.

FIG. 3 is a flowchart illustrating a flow of device registration processing in the information management system according to the first embodiment.

FIG. 4 is a diagram illustrating an example of a screen display of a smartphone of the information management system according to the first embodiment.

FIG. 5 is a diagram illustrating a configuration example of an information management system according to a second embodiment.

FIG. 6 is a flowchart illustrating a flow of device registration processing in the information management system according to the second embodiment.

FIG. 7 is a diagram illustrating an example of a screen display of the smartphone in the information management system according to the second embodiment.

FIG. 8 is a flowchart illustrating a flow of device registration processing in the information management system according to a third embodiment.

FIG. 9A is a first diagram illustrating an example of a change in display of a smartphone in the information management system according to the third embodiment. FIG. 9B is a second diagram illustrating an example of a change in display of the smartphone in the information management system according to the third embodiment.

FIG. 10 is a diagram illustrating an example of a screen display of the smartphone in the information management system according to the third embodiment.

FIG. 11 is a block diagram illustrating an overview of a configuration example of an information management system according to a fourth embodiment.

Figure 12:
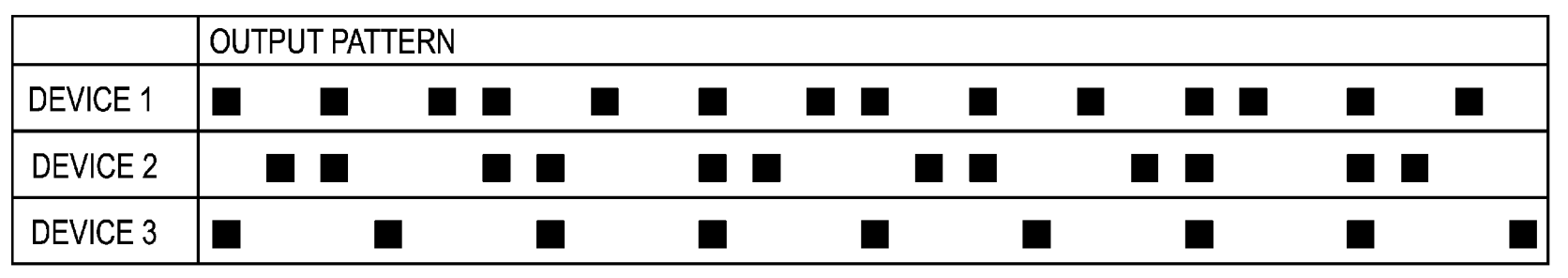

FIG. 12 is an explanatory diagram illustrating an image of a pattern of the present specification.

DESCRIPTION OF EMBODIMENTS

Specific embodiments of the present invention will be described below with reference to the drawings.

First Embodiment

First, an example of the embodiments of the present invention will be described with reference to FIG. 1 to FIG. 5. However, the dimensions, materials, shapes, relative arrangements, and other characteristics of the components described in this embodiment are not intended to limit the scope of this invention unless otherwise indicated.

System Configuration

FIG. 1 is a schematic diagram illustrating a configuration example of a health information management system 1 according to the present embodiment. As illustrated in FIG. 1, the health information management system 1 includes a blood pressure monitor 10 used as an example of a measuring device, and a smartphone 20 used as an example of an information terminal. By device-registering measuring devices including the blood pressure monitor 10 as described below, the smartphone 20 can subsequently identify and acquire measurement information regarding the device-registered devices.

Measuring Device

The blood pressure monitor 10 of the present embodiment is a measuring device that measures the blood pressure of a user using a so-called oscillometric method and as illustrated in FIG. 1, includes a sensor unit 110, a display unit 120, a measuring device speaker 130, an input unit 140, and a measuring device control unit 150.

The sensor unit 110 includes a pressure sensor disposed in a cuff portion of the blood pressure monitor 10, and detects a pulse wave from a blood vessel of the user under an appropriate cuff pressure. The blood pressure monitor 10 of the present embodiment is capable of measuring a pulse in addition to a systolic blood pressure and a diastolic blood pressure on the basis of the pulse wave detected by the sensor unit. The values of the systolic blood pressure, the diastolic blood pressure, and the pulse are collectively referred to as measurement values.

The display unit 120 is formed by, for example, a liquid crystal display, and displays the operating condition of the device and the like as well as calculated measurement values.

The measuring device speaker 130 is an output means capable of generating sound waves, and can output ultrasonic waves as well as sound waves in the audible range.

The input unit 140 is an input means such as a button or a touch panel display that receives input from the user, and receives various operations from the user, such as those for turning the power source on or off, starting measurement, changing a mode, and selecting an item.

The measuring device control unit 150 is a means for controlling the blood pressure monitor 10, and includes a central processing unit (CPU), for example. In response to reception of the execution of the device information registration mode from the user via the input unit 140, the measuring device control unit 150 causes the measuring device speaker 130 to generate ultrasonic waves including identification information regarding the measuring device. Note that the identification information is held by a storage means or the like (not illustrated), for example.

Additionally, the measuring device control unit 150 may cause the display unit 120 to output a display enabling the device registration mode to be determined while the device registration mode is in execution. For example, a "P" mark may be displayed and blinked. FIG. 2 illustrates a display example of the display unit 120 in a pairing mode.

In addition to performing the above-described control, the measuring device control unit 150 controls each component of the blood pressure monitor 10 to execute processing in accordance with the operation of the user via the input unit 140.

Information Terminal

The smartphone 20, used as an example of the information terminal, includes a microphone 210, a touch panel display 220, a storage unit 230, an information terminal control unit 240, and an information terminal speaker 250 as illustrated in FIG. 1.

The microphone 210 is one of the input means of the smartphone 20, and detects sound waves including ultrasonic waves.

The touch panel 220 is used as a display means functioning as one of the output means and is also used as an input means, and as described below, in response to acquisition of the identification information regarding the blood pressure monitor 10 from the ultrasonic waves detected by the microphone 210, the display means of the information terminal displays the information regarding the blood pressure monitor 10 having transmitted the identification information. In addition, operations from the user are received via various input images.

The storage unit 230 includes, for example, a long-term storage medium such as a flash memory, in addition to a main storage device such as a Random Access Memory (RAM), and stores various types of information such as the identification information regarding measuring devices including the blood pressure monitor 10 to be device-registered, application programs, and measurement values.

The information terminal speaker 250 is one output means for outputting sound waves, and outputs various sounds.

The information terminal control unit 240 is a means for controlling the smartphone, and includes, for example, a CPU and the like, and executes various programs stored in the storage unit 230 to deliver functions corresponding to the programs. Specifically, the information terminal control unit 240 detects the ultrasonic waves output by the blood pressure monitor 10 via the microphone 210 to acquire, from the ultrasonic waves, identification information identifying the blood pressure monitor 10. In addition, the touch panel display 220 is caused to display information regarding the blood pressure meter 10 for which the identification information has been acquired.

Method for Device-Registering Measuring Device in Information Terminal

Now, a method for device-registering the blood pressure monitor 10 on the smartphone 20 will be described. FIG. 3 is a flowchart illustrating a processing procedure used when the blood pressure monitor 10 is device-registered on the smartphone 20.

As illustrated in FIG. 3, the user first causes the smartphone 20 to stand by via the touch panel display 220 and the information terminal control unit 240 of the smartphone 20 such that the smartphone 20 is ready for receiving measurement information (step S101). Specifically, for example, an application program for health information management may be executed, and the information terminal control unit 240 may be configured to continually execute the application program in the background.

Then, the user brings the blood pressure monitor 10 into the device registration mode via the display unit 120 and the measuring device control unit 150 of the blood pressure monitor 10 (step S102). In the device registration mode, the measuring device control unit 150 causes the measuring device speaker 130 to output ultrasonic waves (step S103). Note that, as described above, the ultrasonic wave is output including identification information enabling the blood pressure monitor 10 to be identified.

Then, the microphone 210 of the smartphone 20 in an information wait state detects the ultrasonic waves output in step S103 (step S104). Subsequently, the information terminal control unit 240 acquires the identification information regarding the blood pressure monitor 10 included in the ultrasonic waves detected in step S104 (step S105).

Then, the information terminal control unit 240 displays, on the touch panel display 220, information related to the blood pressure monitor 10 for which the identification information has been acquired (step S106), and receives an input indicating that the displayed blood pressure monitor 10 is to be device-registered. Specifically, for example, an operation button may be displayed for confirming that the device displayed on the touch panel display 220 is to be registered. FIG. 4 illustrates a display screen example for receiving the input of the user.

A message section of the screen illustrated in FIG. 4 depicts "DEVICE IS DISPLAYED FOR WHICH DEVICE REGISTRATION CAN BE CURRENTLY ACCEPTED. PLEASE SELECT "OK" TO REGISTER DISPLAYED DEVICE ON SMARTPHONE" That is, the display indicates that the displayed blood pressure monitor 10 is to be device-registered.

When the user provides an input indicating that the displayed measuring device is to be device-registered (step S107), the information terminal control unit 240 causes the storage unit 230 to store the identification information acquired in step S105 (step S108), and terminates the series of steps of processing.

The storage of the identification information in step S108 identifiably registers the specific blood pressure monitor 10 on the smartphone 20, completing the device registration. After such device registration is performed, the information terminal control unit 240 can exclusively acquire measurement values transmitted from the blood pressure monitor 10 transmitting the identification information stored in the storage unit 230.

Note that in the series of flows described above, the processing in step S103 and the processing in step S104 may be performed in reverse order or concurrently.

According to the configuration of the system as described above, to register the measuring device on the information terminal, the operation performed by the user is to simply bring the measuring device and the information terminal into the device registration mode and check whether to register the measuring device displayed on the touch panel display, leading to a very low burden on the user for device registration. Additionally, the identification information is transmitted by using ultrasonic waves output from the speaker, eliminating the need to separately mount a device for near-field wireless communication. This enables a reduction in the cost of devices constituting the system.

Second Embodiment

Now, another embodiment of the present invention will be described with reference to FIG. 5 to FIG. 7. In the following, components that are the same as those in the first embodiment are given the same reference numerals, and detailed descriptions thereof will be omitted.

FIG. 5 is a schematic diagram illustrating a configuration example of a health information management system 2 according to the present embodiment. As illustrated in FIG. 5, the health information management system 2 includes a plurality of blood pressure monitors 10a, 10b, and 10c and the smartphone 20. Note that the components of each of the blood pressure monitors 10a, 10b, and 10c, and the smartphone 20 are similar to those in the first embodiment, and therefore descriptions of the components will be omitted.

The health information management system 2 in the present embodiment, unlike in the first embodiment, includes the plurality of blood pressure monitors, and thus the smartphone 20 may receive measurement information from a blood pressure monitor that is different from the blood pressure monitor to be device-registered by the user. Thus, when the blood pressure monitor 10 is device-registered on the smartphone 20, a procedure different from that of the first embodiment is executed.

FIG. 6 is a flowchart illustrating a processing procedure executed in the health information management system 2 of the present embodiment when the blood pressure monitors 10 is device-registered on the smartphone 20. The processing from step S201 to step S205 is similar to the processing from step S101 to step S106 in the first embodiment. In other words, the user brings the smartphone 20 into a standby state in step S201 and brings the blood pressure monitor 10 into the device registration mode in step S202. Then, the measuring device control unit 150 causes the blood pressure monitor 10 to generate ultrasonic waves including the identification information in step S203. Furthermore, in step S204, the information terminal control unit 240 causes the microphone 210 to detect ultrasonic waves, and in step S205, acquires the identification information included in the ultrasonic waves detected.

Next, the information terminal control unit 240 causes the touch panel display 220 to display a list of blood pressure counters 10 having transmitted the identification information acquired in step S205, and prompts the user to selects one of the devices (step S206). FIG. 7 is an example of a display screen of the touch panel display 220 displaying a list in response to acquisition of the identification information from a plurality of the blood pressure monitors 10. As illustrated in FIG. 7, in a case where identification information is acquired from a plurality of measuring devices, the devices may be listed in order of intensity of sound pressure of the ultrasonic waves by which the identification information is transmitted. The intensity of the sound pressure and the distance to the source of the ultrasonic waves are correlated, and thus more intense sound pressure can be estimated to indicate a closer device. Based on this, which of the blood pressure monitors listed may be selected can be determined from a positional relationship with the blood pressure monitor 10 desired to be registered.

When the user selects any one device from among the blood pressure monitors 10 listed (step S207), the information terminal control unit 240 displays, on the touch panel display 220, information related to the selected blood pressure monitor 10, and receives an input indicating that the displayed blood pressure monitor 10 is to be device-registered. In this case, the user may be prompted to provide an input by using an example of a display screen similar to that illustrated in FIG. 4 in the first embodiment, for example.

When the user provides the input indicating that the displayed measuring device is to be device-registered (step S208), the information terminal control unit 240 causes the storage unit 230 to store the identification information acquired in step S205 (step S209), and terminates the series of steps of processing.

The storage of the identification information in step S209 identifiably registers the specific blood pressure monitor 10 on the smartphone 20, completing the device registration. After such device registration is performed, the information terminal control unit 240 can exclusively acquire measurement values transmitted from the blood pressure monitor 10 transmitting the identification information stored in the storage unit 230.

According to the configuration as described in the present embodiment, in an information management system in which a plurality of measuring devices of the same type are used, even in a case where any measuring devices are in the device registration mode at the same time, the distance to the measuring device to be device-registered can be estimated based on the sound pressure of ultrasonic waves detected by the information terminal. Based on this, the information terminal can select the measuring device to be device-registered.

Modified Example

Note that in the second embodiment described above, in step S206, the blood pressure monitors 10 are listed in order of intensity of sound pressure of the ultrasonic waves detected by the smartphone 20. However, this is not necessary, and for example, the blood pressure monitors may be listed in the order in which the identification information is acquired. In addition, the blood pressure monitors 10 need not necessary be listed, and for example, only the blood pressure monitor 10 for which the detected ultrasonic waves have the most intense sound pressure may be displayed as a first candidate.

Third Embodiment

Now, another embodiment of the present invention will be described with reference to FIG. 8 to FIG. 10. The health information management system according to the present embodiment includes identical components as those of the health information management system according to the first embodiment, but differs in the processing executed for device registration. FIG. 8 is a flowchart illustrating a processing procedure executed in the present embodiment when the blood pressure monitor 10 is device-registered on the smartphone 20.

As illustrated in FIG. 8, the user first causes the smartphone 20 to stand by via the touch panel display 220 and the information terminal control unit 240 of the smartphone 20 such that the smartphone 20 is ready for receiving measurement information (step S301). Specifically, for example, an application program for health information management may be executed, and the information terminal control unit 240 may be configured to continually execute the application program in the background.

Then, the user brings the blood pressure monitor 10 into the device registration mode via the display unit 120 and the measuring device control unit 150 of the blood pressure monitor 30 (step S302). In the device registration mode, the measuring device control unit 150 causes the measuring device speaker 130 to output ultrasonic waves in a unique pattern (step S303). Note that, as described above, the ultrasonic wave is output including identification information enabling the blood pressure monitor 10 to be identified.

Furthermore, the measuring device control unit 150 causes the measuring device speaker 130 to generate a signal sound with a beat linked with the pattern (step S304). Note that in this case, the measuring device control unit 150 may cause the display unit to output display that varies in the same pattern as that described above. Furthermore, the LED light (not illustrated) may be caused to blink in accordance with the pattern.

Then, the microphone 210 of the smartphone 20 in the information wait state detects the ultrasonic waves output in step S303 (step S305). Subsequently, the information terminal control unit 240 acquires the identification information regarding the blood pressure monitor 10 included in the ultrasonic waves detected in step S305 (step S306).

Then, the information terminal control unit 240 displays, on the touch panel display 220, information related to the blood pressure monitor 10 for which the identification information has been acquired (step S307), and outputs, to the touch panel display 220, image display that varies in the same pattern as that of the sound (and other outputs) output from the blood pressure monitor 10 (step S308). Note that, at this time, the information terminal control unit 240 may cause the information terminal speaker 250 to output sound in the same pattern as that described above, or may cause another output means not illustrated to generate an output in the same pattern as that described above. Specifically, for example, the LED light may be caused to blink in the same pattern as that described above, or the vibration device may be caused to vibrate in the same pattern as that described above. FIG. 9 illustrates an example of a case in which a variation in animation exhibiting a pattern is displayed on the touch panel display 220. FIG. 9A is a diagram illustrating an example of a display screen for timing involving no output, and FIG. 9B is a diagram illustrating an example of a display screen for timing involving output, and illustrating the simultaneous turn-on of the LED light in the touch panel display 220.

Furthermore, the information terminal control unit 240 prompts the user to provide an input indicating that the output pattern of the sound output from the blood pressure monitor 10 is identical to the variation pattern of the display of the touch panel display 220 of the smartphone 20 (and other outputs) in a case where the identicalness is confirmed (step S309). Specifically, for example, the touch panel display 220 may be caused to display an operation button for providing an input indicating that the patterns match. FIG. 10 illustrates an example of a display screen for receiving the input of the user in step S309.

A message section of the screen illustrated in FIG. 10 depicts "DEVICE IS DISPLAYED FOR WHICH DEVICE REGISTRATION CAN BE CURRENTLY ACCEPTED. PLEASE SELECT "OK" IF DISPLAYED DEVICE AND SMARTPHONE PROVIDE SAME OUTPUT PATTERN. DEVICE IS TO BE REGISTERED IN SMARTPHONE" In other words, in a case where an input is provided indicating that the output pattern from the blood pressure monitor 10 is identical to the output pattern from the smartphone 20, information is provided that indicates that the blood pressure monitor 10 is registered on the smartphone 20.

In step S309, after receiving the input indicating that the output pattern of the sound output from the blood pressure monitor 10 is identical to the variation pattern of display of the touch panel display 220 of the smartphone 20, the information terminal control unit 240 causes the storage unit 230 to store the identification information acquired in step S306 (step S310), terminating the series of steps of processing.

The storage of the identification information in step S310 identifiably registers the specific blood pressure monitor 10 on the smartphone 20, completing the device registration. After such device registration is performed, the information terminal control unit 240 can exclusively acquire measurement values transmitted from the blood pressure monitor 10 transmitting the identification information stored in the storage unit 230.

Note that in the series of flows described above, the processing in step S303 and the processing in step S304 may be performed in reverse order or concurrently.

According to the configuration of the system as described above, in order to register the measuring device on the information terminal, the user may simply bring the measuring device and the information terminal into the device registration mode and check whether the measuring device and the information terminal output the identical pattern, leading to a very low burden on the user for device registration. In addition, the pattern is output in a human perceivable manner, and thus the user can determine whether the measuring device being device-registered through the information terminal is really the device the user likes to device-register, allowing an uneasy feeling of the user to be removed. Furthermore, the identification information is transmitted by using ultrasonic waves output from the speaker, eliminating the need to separately mount an apparatus for near-field wireless communication. This enables a reduction in the cost of devices constituting the system.

Fourth Embodiment

Here, yet another embodiment of the present invention will be described based on FIG. 11. In the following, components that are the same as those in the first embodiment are given the same reference numerals, and detailed descriptions thereof will be omitted. FIG. 11 is a schematic diagram illustrating a configuration example of a health information management system 3 according to the present embodiment. As illustrated in FIG. 11, the health information management system 3 includes a blood pressure monitor 30 used as an example of the measuring device, and a smartphone 40 used as an example of the information terminal.

The blood pressure monitor 30 differs from the blood pressure monitor 10 according to the first embodiment in that the blood pressure monitor 30 includes a measuring device communication unit 360, and is otherwise similar to the blood pressure monitor 10. Additionally, the smartphone 40 also differs from the smartphone 20 of the first embodiment in that the smartphone 40 includes an information terminal communication unit 460, and is otherwise similar to the smartphone 20.

Each of the measuring device communication unit 360 and the information terminal communication unit 460 is a communication antenna for bidirectional wireless communication such as Bluetooth, and the blood pressure monitor 30 and the smartphone 40 are configured to enable wireless communication via the respective communication units. Such a configuration allows the blood pressure monitor 30 and the smartphone 40 to communicate wirelessly with each other in both directions and to be paired with each other.

However, Bluetooth does not necessarily involve reception of intense electromagnetic waves from nearby devices, and has a wide communicable range compared to ultrasonic waves. Thus, when a plurality of devices of the same type as that of a device to be registered are included within a communication range, the user has difficulty in determining which of the devices is to be registered.

Thus, instead of searching for a pairing partner by Bluetooth advertising, the blood pressure monitor 30 and smartphone 40 in the present embodiment use a method similar to the method in the first embodiment to determine the blood pressure monitor 30 to be device-registered on the smartphone 40.

Specifically, the blood pressure monitor 30 outputs ultrasonic waves including identification information, and the smartphone 40 detects the ultrasonic waves, acquires, from the ultrasonic waves, the identification information regarding the blood pressure monitor 30, and displays, on the touch panel display 220, information related to the blood pressure monitor 30. The user provides the smartphone 40 with an input indicating that the displayed blood pressure monitor 30 is to be device-registered, determining the blood pressure monitor 30 to be a pairing partner. After pairing is thus established between the blood pressure monitor 30 and the smartphone 40, wireless communication via the measuring device communication unit 360 and the information terminal communication unit 460 enables bidirectional information communication between the blood pressure monitor 30 and the smartphone 40.

According to the configuration as described in the present embodiment, even in a case where a plurality of measuring devices are provided, searching for a pairing partner using ultrasonic waves enables the information terminal to determine a device to be paired based on the relationship between the intensity of the sound pressure and the distance to the pairing target, allowing the measuring device and the information terminal to be paired. Furthermore, connection enabling bidirectional information communication can be established between the measuring device and the information terminal.

Other

The description of each of the examples described above is merely illustrative of the present invention, and the present invention is not limited to the specific embodiments described above. Within the scope of the technical idea of the present invention, various modifications and combinations may be made.

For example, the measuring device may be a body information measuring device other than a blood pressure monitor, such as a scale, a body composition meter, a pulse meter, or a thermometer. Additionally, the measuring device may be an activity meter that measures the quantity of exercise in a pedometer, a tread mill, an Aerobike (trade name), or the like. In this case, the measured quantity displayed on the display unit may be the number of steps, a travel (walking) distance, or the like, may be a value such as the estimated number of calories consumed, or both. Additionally, the measuring device may be an environment sensor device that measures environmental information such as room temperature, humidity, noise, and illuminance. Note that while, in the example described above, the system includes only one type of measuring device that is the blood pressure monitor, the system may be configured to include a plurality of different measuring devices.

Additionally, the information terminal is not limited to a smartphone, and may be another mobile information terminal such as a tablet terminal, or may be a stationary terminal. Additionally, the communication unit in the third embodiment is not limited to a communication unit intended for Bluetooth communication, and may be an antenna enabling other wireless communication such as infrared communication.

Additionally, the blood pressure monitor 30 and the smartphone 40 according to the fourth embodiment may be applied to the information management system in the second embodiment.

REFERENCE SIGNS LIST 1, 2, 3 Information management system
10, 30 Blood pressure monitor
110 Sensor unit
120 Display unit
130 Measuring device speaker
140 Input unit
150 Measuring device control unit
20, 40 Smartphone
210 Microphone
220 Touch panel display
230 Storage unit
240 Information terminal control unit
250 Information terminal speaker
360 Measuring device communication unit
460 Information terminal communication unit

The invention claimed is:

1. An information management system comprising one or more measuring devices and one or more information terminals, wherein
the measuring device includes:
a measuring device output device including an oscillation device capable of generating at least ultrasonic waves in a unique pattern; and
a measuring device processor configured to:
use the ultrasonic waves generated by the oscillation device to transmit measuring device information including identification information identifying the measuring device, and
cause the measuring device output device to generate a human-perceivable output in a pattern identical to the unique pattern,
the information terminal comprises:
an input device including a microphone capable of detecting the ultrasonic waves, an information terminal output device including at least a display, a storage, and an information terminal processor,
the information termal processor configured to:
acquire, via the microphone, the identification information from the ultrasonic waves in the unique pattern output from the measuring device,
cause the display of the information terminal to display the measuring device having transmitted the identification information acquired,
cause the information terminal output device to generate a human-perceivable output in a pattern identical to the pattern of the output from the measuring device displayed on the display of the information terminal, receive, via the input device, an input indicating that the measuring device displayed on the display of the information terminal is to be registered on the information terminal, use, as the input indicating the registration of the measuring device on the information terminal, reception, via the input device, of an input indicating that an occurrence pattern of the output from the measuring device displayed on the display of the information terminal is identical to an occurrence pattern of the output from the information terminal, and cause the storage to store the identification information regarding the measuring device for which the input indicating registration of the measuring device on the information terminal has been provided.

2. The information management system according to claim 1, wherein
the measuring device information includes a measurement value obtained by the measuring device.

3. The information management system according to claim 1, wherein
in a case of acquiring the identification information regarding a plurality of the measuring devices, the information terminal processor is further configured to cause, in response to acquisition of the identification information, the display to preferentially display the measuring device for which ultrasonic waves with a more intense sound pressure have been detected by the microphone.

4. The information management system according to claim 1, wherein
the measuring device output device includes a sound wave generator capable of outputting sound waves in an audible range, and
the measuring device processor is further configured to cause the sound wave generator to output ultrasonic waves in the unique pattern and to generate the sound waves in the audible range in an identical pattern.

5. The information management system according to claim 1, wherein
the measuring device further includes a display, and
the measuring device processor is further configured to cause the sound wave generator to generate the ultrasonic waves in the unique pattern, and vary display of the display in a pattern identical to the unique pattern.

6. The information management system according to claim 1, wherein
the information terminal processor is further configured to vary display of the display of the information terminal in a pattern identical to the unique pattern.

7. The information management system according to claim 1, wherein
the information terminal output device includes sound wave generator capable of generating sound waves in the audible range, and the information terminal processor is further configured to cause the sound wave generator of the information terminal to generate the sound waves in the audible range in a pattern identical to the unique pattern.

8. The information management system according to claim 1, wherein
the information terminal output device includes a vibration device vibrating the information terminal, and
the information terminal processor is further configured to cause the information terminal to vibrate in a pattern identical to the unique pattern.

9. The information management system according to claim 1, wherein
the measuring device and the information terminal each include a wireless communication unit, including an antenna, capable of transmitting and receiving information from each other and device-register each other via the wireless communication unit.

10. The information management system according to claim 1, wherein
the measuring device is one of a scale, a body composition meter, a blood pressure monitor, a pulse meter, a thermometer, and an activity meter.

11. The information management system according to claim 1, wherein
the information terminal is a smartphone.

12. A method for device registration of a measuring device on an information terminal, the method comprising the steps of:
the measuring device generating ultrasonic waves in a unique pattern to transmit measuring device information including identification information identifying the measuring device;
the measuring device outputting a human-perceivable output in a pattern identical to the unique pattern;
the information terminal detecting the ultrasonic waves in a unique pattern;
the information terminal acquiring the identification information from the ultrasonic waves in a unique pattern;
the information terminal displaying the measuring device having transmitted the identification information acquired;
the information terminal outputting the unique pattern, which is a human-perceivable output and is the same as that output from the displayed measuring device;
the information terminal registering the displayed measuring device on the information terminal by receiving an input indicating that the unique pattern outputted from the displayed measuring device and the unique pattern outputted from the information terminal are the same; and
the information terminal storing the identification information regarding the measuring device for which the input indicating registration of the measuring device on the information terminal has been provided.

* * * * *